United States Patent [19]

Kaya et al.

[11] Patent Number: 4,574,626
[45] Date of Patent: Mar. 11, 1986

[54] ENTHALPY MEASUREMENT FOR TWO PHASE SUBSTANCE

[75] Inventors: Azmi Kaya, Akron; Marion A. Keyes, IV, Chagrin Falls, both of Ohio

[73] Assignee: The Babcock & Wilcox Company, New Orleans, La.

[21] Appl. No.: 592,499

[22] Filed: Mar. 23, 1984

[51] Int. Cl.[4] .................... G01K 17/00; G01N 7/00; G01N 9/00
[52] U.S. Cl. ......................... 73/112; 374/35; 374/31; 73/115; 364/557; 364/558; 364/499
[58] Field of Search ............. 374/31, 42, 35; 364/556, 557, 558, 499; 73/112, 115

[56] References Cited

U.S. PATENT DOCUMENTS

| | | | |
|---|---|---|---|
| 3,866,026 | 2/1975 | Vivy | 364/556 |
| 3,970,832 | 7/1976 | Itschner | 364/497 |
| 4,078,431 | 3/1978 | Mott | 374/31 |

FOREIGN PATENT DOCUMENTS 58-120157  7/1983  Japan ...................... 374/35

Primary Examiner—Kenneth M. Schor
Attorney, Agent, or Firm—Vytas R. Matas; Robert J. Edwards

[57] ABSTRACT

An enthalpy measuring arrangement for measuring the heat content of a substance which may in the liquid phase, vapor phase or a mixed phase of liquid and vapor, comprises a first enthalpy calculating module for calculating the enthalpy of the substance when in a two-phase condition utilizing a plurality of discrete function blocks. The specific volumes of the overall mixture is calculated using a density transmitter which measures the density of the substance. Tables are utilized to obtain the specific volumes of the gas and vapor part of the substance on the basis of a measured temperature for the substance. These values are in turn used to obtain a quality value which is multiplied by a value representing the difference between the enthalpys of the vapor and liquid components of the substance to obtain the overall enthalpy of the mixture. Another module with a plurality of function blocks generates the enthalpy of the substance when it is superheated or entirely in the vapor phase. A selector module is connected to the mixed and vapor phase calculating modules to determine which of the modules should be utilized and to calculate the overall enthalpy of the substance regardless of its phase.

5 Claims, 5 Drawing Figures

ENTHALPY MEASUREMENT FOR TWO PHASE SUBSTANCE

FIELD AND BACKGROUND OF THE INVENTION

The present invention relates in general to equipment for measuring thermodynamic properties of a substance and, in particular to a new and useful enthalpy measuring arrangement for measuring enthalpy or heat content of a two-phase substance which may be in the form of a gas, a liquid, or a mixture of gas plus liquid.

The thermodynamic properties of substances are normally calculated using computer algorithms with high level computer languages. While discrete function blocks have been utilized to calculate the enthalpy of a superheated or totally gaseous substance, only computers have hitherto been utilized to measure the enthalpy of a two-phase substance. The use of function blocks to measure the enthalpy of a gaseous substance is disclosed in U.S. Pat. No. 4,244,216 issued Jan. 13, 1981.

The use of computers programmed with high level language to calculate the enthalpy of two-phase saturated substances, is slow in processing time while also requiring highly trained personnel. This results in a high cost factor for such calculations.

SUMMARY OF THE INVENTION

The present invention is drawn to an enthalpy measuring arrangement which utilizes function blocks to measure enthalpy of a two-phase substance without the use of computers. The performance of function blocks is equivalent in effectiveness to that of computers yet the calculations are performed at a much higher speed. Essentially the advantages of analog devices and the advantages of computers are combined in the present invention. The use of simple function blocks that are assembled in a skillful manner provide the calculations without the need for a computer or a computer program.

The present invention can apply to any substance which does or can exist in two phases, in particular a liquid and vapor phhase. Such substances include Freon, steam, mercury vapor, ammonia vapor, or other substances that can be used for example as a refrigerant or heating medium. A specific example of the invention used for measuring the enthalpy of a stream of Freon-12 is disclosed.

The inventive arrangement utilizes selector logic for choosing an appropriate enthalpy measuring module depending on the state of the substance, specifically whether it is liquid, vapor, or two-phase.

According to the invention, a temperature a pressure and a density measurement are utilized in conjunction with the tables of known properties for the specific substance to calculate the enthalpy or heat content of the substance. For Freon-12 such tables can be found for example, in *Fundamentals of Classical Thermodynamics*, Van Wylen and Soonntag, by J. Wiley, 1973. Other published tables are also available fo enthalpys of different substances at known conditions, as well as other properties such as specific volume and pressures at known conditions. See for example the tables that are available from Keenan and Keyes, "Thermodynamic Properties of Steam".

Accordingly, an object of the present invention is to provide an enthalpy measuring arrangement for measuring the enthalpy of a substance which can be in a two-phase condition, that utilizes function blocks combined in a particular manner to avoid the use of computers or computer programs.

A further object of the invention is to provide such a measuring arrangement which comprises a first enthalpy calculating module for calculating the enthalpy of the substance in two-phases including a mixture of vapor and liquid substance, a second enthalpy calculating module for calculating the enthalpy of the substance in a superheated or vapor phase and a selector module for selecting which of the calculating modules is utilized to determine the total enthalpy or whether both of the modules are utilized.

A further object of the invention is to provide an enthalpy measuring arrangement which is capable of measuring the enthalpy of a two phase substance utilizing a measured quantity for density or temperature of the substance as well as table values for enthalpys at known conditions to calculate the enthalpy of the mixed vapor and liquid phase substance.

A still further object of the invention is to provide an enthalpy measuring arrangement which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

Where used in the claims, "connected" means electrically connected, or by some other similar means of transmission, so that a signal can be received and operated upon.

DESCRIPTION OF THE PREFERRED EMBODIMENT

Figure 1:
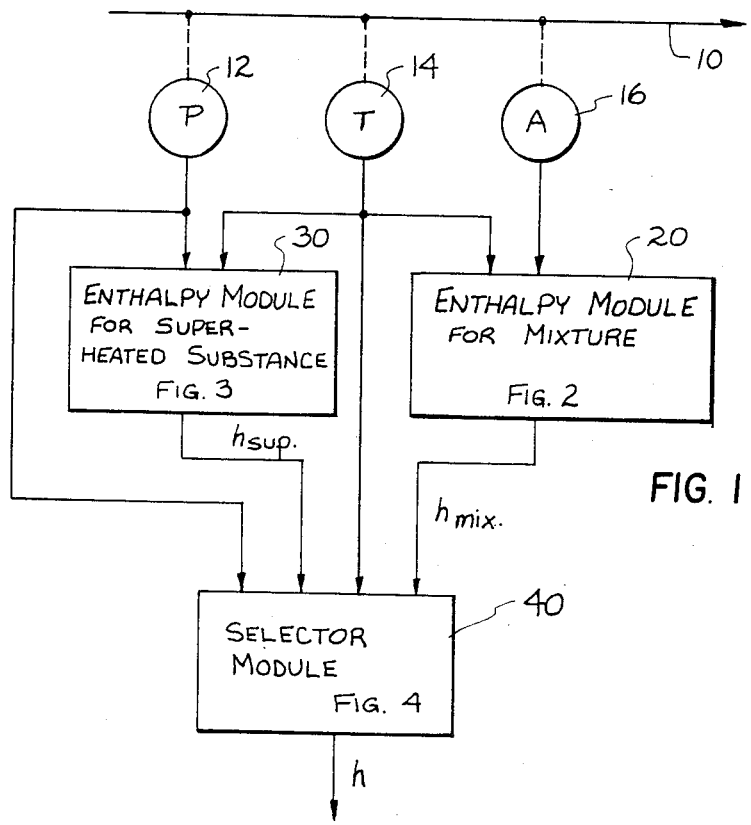
FIG. 1 is a block diagram showing the overall enthalpy measuring arrangement of the invention.

Referring to the drawings in particular, the invention embodied in FIG. 1 comprises an enthalpy measuring arrangement for measuring the enthalpy of a substance in a line 10 which may be in the vapor, liquid or two-phase state including a mixture of vapor and liquid. In the embodiment illustrated, the substance is assumed to be Freon-12.

A pressure P of the substance in line 10 is taken by a pressure transmitter 12. The temperature T of the substance is taken by a temperature transmitter 14 and the density A of the substance is measured in a density transmitter 16. Transmitters 12,14 and 16 are of known design so that further details are not here provided. Suffice it to say they transmit signals which correspond to the parameter being measured.

The temperature and density measurements are utilized in an enthalpy calculating module 20 which, as will be described in greater detail hereinunder, generates a value corresponding to the enthalpy of the two-phase or mixed substance ($h_{mix}$).

A second enthalpy measuring module 30 utilizes the measured temperature and pressure to calculate an enthalpy value ($h_{sup}$) of a fully saturated or vapor phase substance.

The calculated saturated and mixed enthalpys are provided to a selector module 40 along with the measured temperature and pressure values for generating an overall enthalpy value (h) for the substance in line 10 whether it be vapor, liquid, or two-phase substance.

Figure 3:
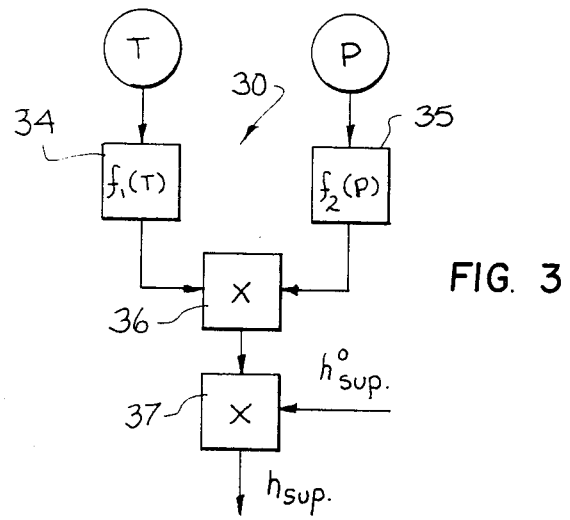
FIG. 3 is a block diagram showing the details of an enthalpy module for measuring the enthalpy of a superheated or vapor phase substance.
Figure 2:
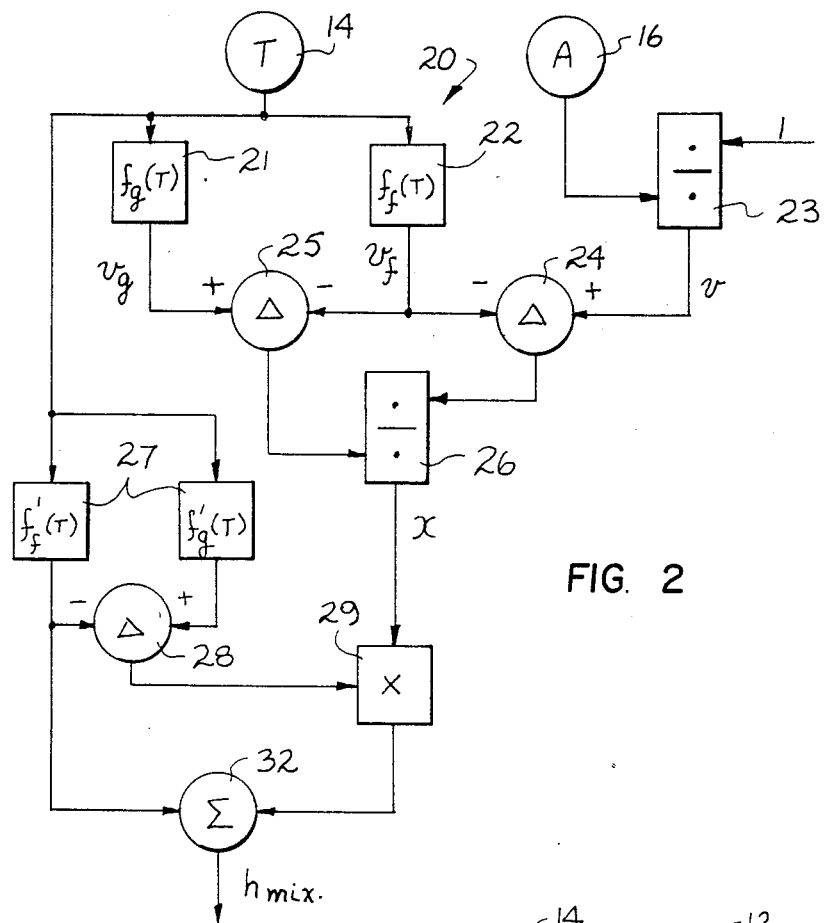
FIG. 2 is a block diagram showing the details of an enthalpy module for measuring the enthalpy of a two-phase mixture.
Figure 4:
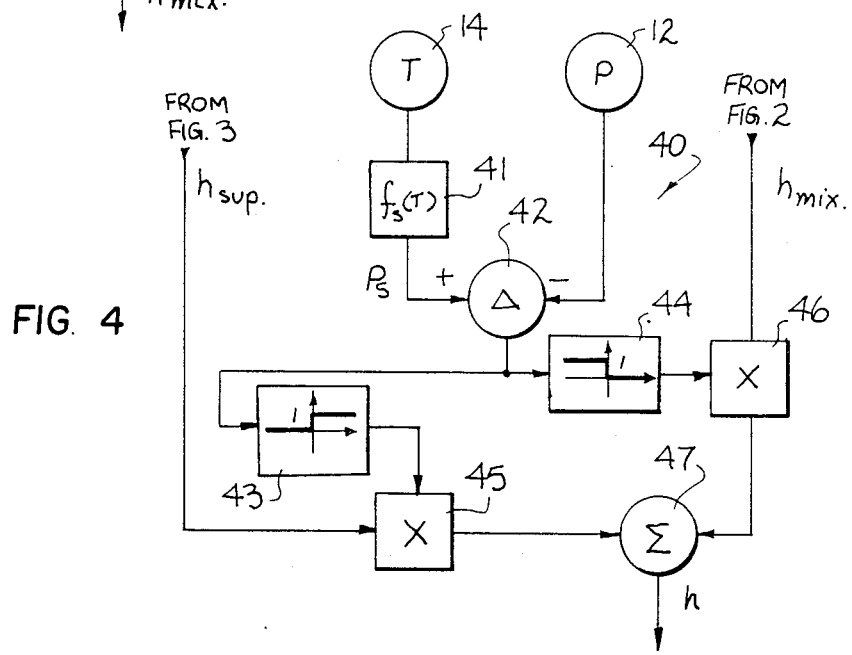
FIG. 4 is a block diagram showing a selector module for selecting which of the enthalpy measurements are to be used in calculating the overall enthalpy of the substance.

FIGS. 2, 3 and 4 show details of the modules 20,30 and 40 respectively. Before discussing these details, however, the calculations and considerations underlying the present invention will first be discussed.

In considering any substance in a mixed or two-phase state, the following holds true:

$$v = v_f + x(v_g - v_f) \quad (1)$$

$$x = (v - v_f)/(v_g - v_f) \quad (2)$$

where:
v = the specific volume of the mixture,
$v_f$ = the specific volume of the saturated liquid part of the mixture,
$v_g$ = the specific volume of the saturated vapor part of the substance, and
x is the quality of interest.

The functional relationships and measurements which determine the specific volumes are as follows:

$$v_f = f_f(T) \quad (3)$$

$$v_g = f_g(T) \quad (4)$$

$$v = 1/A \quad (5)$$

The liquid and vapor specific volumes $v_f$ and $v_g$ can be found from published tables. An example of the values for $v_g$ is illustrated in one of the curves in FIG. 5. The temperature T is provided by the transmitter 14. The specific volume v of the mixture can be calculated using the density transmitter 16.

Utilizing equations (2) through (5) and substituting:

$$x = (1/A - f_f(T))/(f_g(T) - f_f(T)) \quad (6)$$

FIG. 2 illustrates the function blocks which can be utilized to calculate equation (6).

The temperature transmitter 14 is connected to function blocks 21 and 22 which calculate the liquid and vapor specific volumes. The reciprocal of the density is obtained in divider unit 23. Difference or subtraction units 24 and 25 are used to obtain the numerator and denominator in the right hand factor of equation (6) and the division operation takes place in divider unit 26 to obtain the quality value x.

The enthalpy of the mixture $h_{mix}$ can be calculated as follows:

$$h_{mix} = h_f + x(h_g - h_f) \quad (7)$$

Again using tables and functional relationships the liquid component enthalpy $h_f$ and vapor component enthalpy $h_g$ can be found using tables and the temperature from transmitter 14 as follows:

$$h_f = f_f(T) \quad (8)$$

$$h_g = f_g(T) \quad (9)$$

Substituting:

$$h_{mix} = f_f(T) + x[f_g(T) - f_f(T)] \quad (10)$$

Equation (10) can be calculated in the module of FIG. 2 using function blocks 27, subtracting unit 28, multiplication unit 29 and summing unit 32.

It should be noted that this calculation includes the case where the substance is entirely in the liquid phase. In this instance x=zero since $v = v_f$.

FIG. 3 illustrates the second enthalpy module. This module calculates the enthalpy $h_{sup}$ of the superheated or vapor phase substance using function blocks 34 and 35, multiplication unit 36 and multiplication unit 37 as well as the temperature pressure values from transmitters 14 and 12. The method of obtaining the vapor substance enthalpy is fully disclosed in the above mentioned U.S. Pat. No. 4,244,216 which is here incorporated by reference.

Function generator 35 generates a value corresponding to a composite pressure correction factor and function generator 34 generates a value corresponding to a composite temperature correction factor. These are a function of pressure and temperature respectively. The factors are multiplied together in multiplier 36 to produce a compound correction factor which is then multiplied by a known enthalpy $h_{sup}°$, corresponding to enthalpy of the substance at known conditions, to produce the enthalpy of the vapor $h_{sup}$ under the conditions determined by the pressure and temperature transmitters.

The enthalpy of the mixed (including all liquid phase) and vapor phase substance are then supplied to the selector module of FIG. 4 along with signals from the temperature and pressure transmitters 14 and 12.

The selector module 40 determines the state of the substance and uses the appropriate enthalpy module 20 or 30 to calculate the enthalpy h. The functional relationship is:

$$P_s = f_s(T) \quad (11)$$

Figure 5:
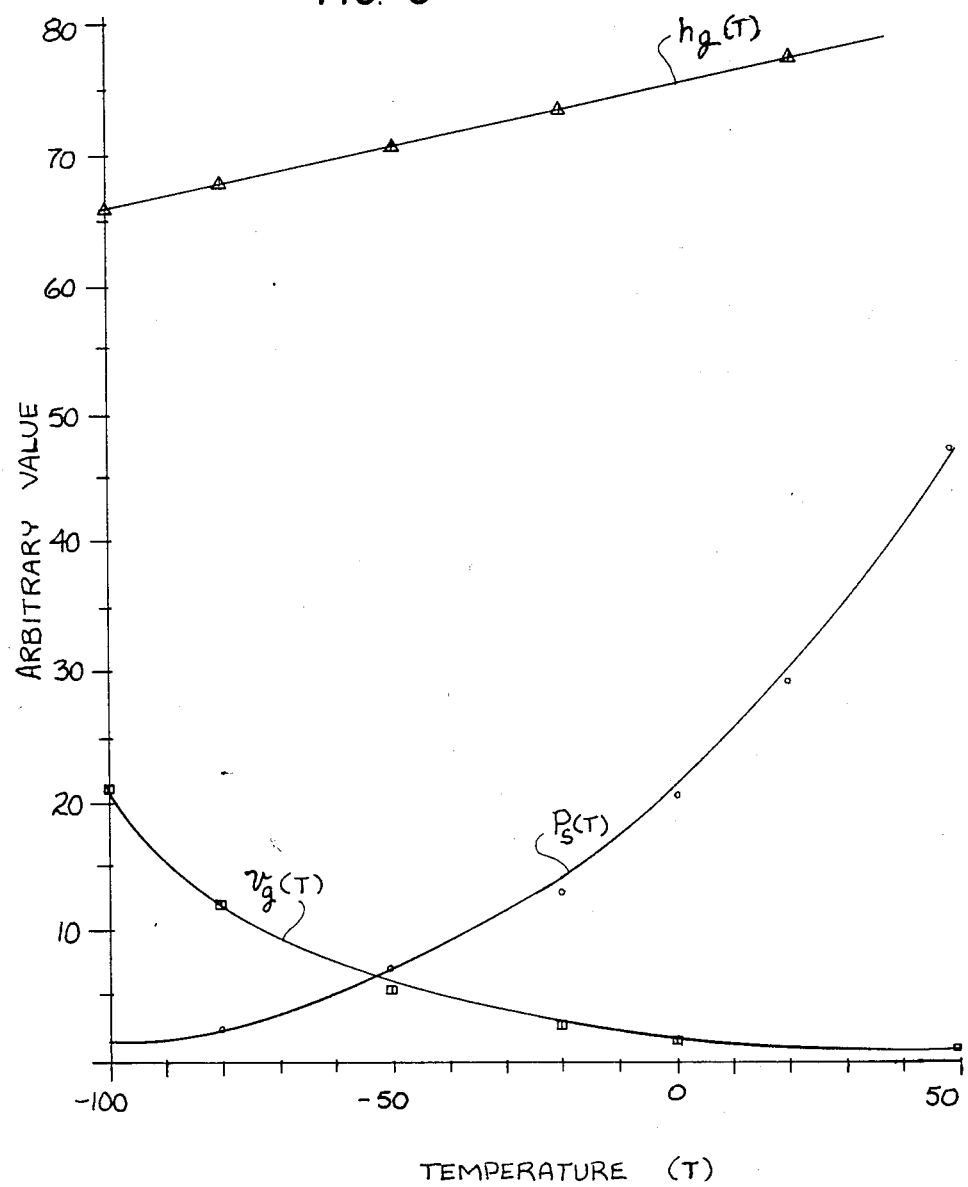
FIG. 5 is a graph representing tabulated values for specific volume, enthalpy and pressure at known temperatures for Freon-12.

The saturated pressure $P_s$ is a function of temperature and can be obtained from a table, or as illustrated in FIG. 5, from a curve of known saturated pressure at known conditions.

The saturated pressure is obtained in function block 41 in FIG. 4. This value is compared with the actual measured pressure from transmitter 12 in a comparator or difference unit 42. Difference unit 42 generates a signal which depends on the attainment or non-attainment of the saturated pressure value. This signal drives value blocks 43 and 44 which generate a one or a zero. These values are multiplied in multiplication units 45 and 46 by the output of the modules in FIGS. 3 and 2 respectively. The results are combined in a summing unit 47 whose output is the enthalpy measurement h.

While a specific embodiment of the invention has been shown and described in detail to illustrate the application of the principles of the invention, it will be understood that the invention may be embodied otherwise without departing from such principles.

What is claimed is:

1. An enthalpy measuring arrangement for measuring the enthalpy of a substance which can be in a two-phase condition, comprising:
   temperature measuring means for measuring the temperature of the substance, and establishing a signal indicative thereof;
   temperature transmitting means for transmitting the signal corresponding to the measured temperature of the substance;
   density measuring means for measuring the density of the substance, and establishing a signal indicative thereof;
   density transmitting means for transmitting the signal corresponding to the measured density of the substance;
   means for providing said substance to said temperature measuring means and said density measuring means, such that temperature and density can be measured;
   a first enthalpy calculating module connected to said temperature transmitting means and to said density transmitting means for calculating the enthalpy of the substance in a two-phase condition as a function of the measured temperature, the measured density and table values for specific volume of the vapor portion of the substance, specific volume for the liquid portion of the substance, enthalpy of the vapor portion of the substance and enthalpy for the liquid portion of the substance, under known conditions.

2. An arrangement according to claim 1, including:
   a second enthalpy calculating module for calculating the enthalpy of the substance in a vapor phase only;
   pressure measuring means for measuring the pressure of the substance, and establishing a signal indicative thereof;
   means for providing said substance to said pressure measuring means, such that pressure can be measured;
   pressure transmitting means for transmitting the signal corresponding to the measured pressure of the substance, connected to said second enthalpy calculating module; and
   a selector module connected to said temperature transmitting means, said first enthalpy calculating module and said second enthalpy calculating module for calculating the enthalpy of the substance in a one-phase and in a two-phase condition, said selector module including value generating means connected to said temperature transmitting means and said pressure transmitting means for generating a zero or one value as a function of the temperature and pressure values depending on whether the substance is in a one-phase or two-phase condition, and to multiply an output of said first and said second module by one of a one and a zero.

3. An arrangement according to claim 2, wherein said first enthalpy calculating module is comprised of:
   a first function block connected to said temperature transmitting means for generating a value as a function of the temperature of the substance corresponding to the specific volume of the vapor in the substance;
   a second function block connected to said temperature transmitting means for generating a value as a function of the temperature of the substance corresponding to the specific volume of the liquid in the substance;
   a first divider unit connected to said density transmitting means for obtaining the reciprocal of the density which corresponds to the specific volume of the overall substance;
   a first subtraction unit connected to said first and second functionblocks for obtaining a difference between the vapor and liquid specific volumes;
   a second subtraction unit connected to said second function block and said first divider unit for obtaining a difference between the liquid and overall specific volumes, and
   a second divider unit connected to said first and said second subtraction units for obtaining a quality value which is a factor of the enthalpy of the substance in a two-phase condition.

4. An arrangement according to claim 3, including:
   a third function block connected to said temperature transmitting means for obtaining an enthalpy of the liquid portion of the substance as a function of the temperature of the substance;
   a fourth function block connected to said temperature transmitting means for obtaining an enthalpy of the vapor portion of the substance as a function of the temperature of the substance;
   a third subtraction unit connected to said third and fourth function blocks for obtaining a difference between the enthalpys of the vapor and liquid portion of the substance;
   a multiplication unit connected to said second divider unit and said third subtraction unit for multiplying the quality by the difference between the enthalpys, and
   a summing unit connected to said fourth function block and said multiplication unit for obtaining the enthalpy of the substance in a two-phase condition.

5. An arrangement according to claim 4, including:
   a second enthalpy calculating module for calculating the enthalpy of the substance in a vapor phase only;
   pressure transmitting means for transmitting the signal corresponding to the measured pressure of the substance, connected to said second module and to a selector module, and
   a selector module connected to said temperature transmitting means, said pressure transmitting means, said first module and said second module for calculating the enthalpy of the substance in a one-phase and a two-phase condition, said selector module including value generating means connected to said temperature transmitting means and said pressure transmitting means for generating a zero or one value as a function of the temperature and pressure values depending on whether the substance is in a one-phase or two-phase condition to multiply an output of said first and said second modules by one of a one and a zero.

* * * * *